US00PP28672P3

(12) United States Plant Patent
Wood

(10) Patent No.: US PP28,672 P3
(45) Date of Patent: Nov. 21, 2017

(54) ***HYDRANGEA* PLANT NAMED 'SMNMAKTSR'**

(50) Latin Name: ***Hydrangea* hybrid**
Varietal Denomination: SMNMAKTSR

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 63 days.

(21) Appl. No.: 14/756,864

(22) Filed: Oct. 22, 2015

(65) Prior Publication Data

US 2017/0118897 P1 Apr. 27, 2017

(51) Int. Cl.
*A01H 5/02* (2006.01)

(52) U.S. Cl.
USPC ..... Plt./250

(58) Field of Classification Search
USPC ..... Plt./250
See application file for complete search history.

(56) References Cited

PUBLICATIONS

Midwest Groundcovers Tuff Stuff Red Mountain *Hydrangea,* retrieved on Feb. 2, 2017, retrieved from the Internet at <http://www.midwestgroundcovers.com/plant/Hydrangea-serrata-SMNMAKTSR> 2 pp.*

Proven Winners Tuff Stuff Red *Hydrangea* Proven Winners.jpg, retrieved on Feb. 2, 2017, retrieved from the Internet at <https://www.provenwinners.com/images/tuff-stuff-red-hydrangea-proven-winnersjpg> 2 pp.*

Reed et al. *Hydrangea macrophylla* and *serrata*—Should we lump 'em or split 'em? SNA Research Conference, vol. 51 (2006) pp. 573-576.*

Upov Pluto Plant Variety Database Feb. 1, 2017 for *Hydrangea* 'Smnmaktsr', retrieved on Feb. 6, 2017, retrieved from the Internet at <https://www3.wipo.int/pluto/user/en/index.jsp> one page.*

* cited by examiner

*Primary Examiner* — June Hwu
(74) *Attorney, Agent, or Firm* — Cassandra Bright

(57) ABSTRACT

A new and distinct *Hydrangea* cultivar named 'SMNMAKTSR' is disclosed, characterized by large lacecap inflorescence with single and double florets. Double florets are bright magenta/pink with yellow/green centers. Plants are cold hardy, with frost resistant flower buds and have a compact growth habit. The new variety is a *Hydrangea*, normally produced as an ornamental plant for containers or gardens.

2 Drawing Sheets

Latin name of the genus and species: *Hydrangea* hybrid. Variety denomination: 'SMNMAKTSR'.

BACKGROUND OF THE INVENTION

The new *Hydrangea* cultivar is a product of a planned breeding program conducted by the inventor, Timothy Wood, in Grand Haven, Mich. The objective of the breeding program was to produce hardy new *Hydrangea* varieties with a compact growth habit, reblooming plants with new flower types and colors. The open pollination resulting in this new variety was made during 2004.

The seed parent is the unpatented commercial variety *Hydrangea serrata* 'Maiko' The pollen parent is unknown, as it was an open pollination breeding program. The new variety was identified as a potentially interesting selection June of 2007, at a greenhouse in Grand Haven, Mich.

Asexual reproduction of the new cultivar 'SMNMAKTSR' by softwood cuttings was first performed during the June of 2007, at commercial greenhouse in Grand Haven, Mich. Subsequent propagation has shown that the unique features of this cultivar are stable and reproduced true to type in 5 successive generations.

SUMMARY OF THE INVENTION

The cultivar 'SMNMAKTSR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNMAKTSR' These characteristics in combination distinguish 'SMNMAKTSR' as a new and distinct *Hydrangea* cultivar:

1. Compact growth habit.
2. Hardy, frost resistant flower buds.
3. Re-blooming plants.
4. Large lace cap flowers.
5. Single and double florets, bright magenta/pink with yellow/green centers on double florets.

PARENT COMPARISON

Plants of the new cultivar 'SMNMAKTSR' are similar to plants of the seed parent, *Hydrangea serrata* 'Maiko' in most horticultural characteristics, however, plants of the new cultivar 'SMNMAKTSR' differ in the following:

1. Single and double florets. The seed parent has only single florets.
2. Magenta pink florets, with centers of double florets colored yellow and green. The seed parent has lighter lavender solid colored florets.
3. The new variety produces larger blooms.

Pollen parent unknown as this is a product of open pollination.

COMMERCIAL COMPARISON

'SMNMAKTSR' can be compared to the patented commercial variety *Hydrangea serrata* 'MAK20', U.S. Plant Pat. No. 24,820. These varieties are similar in most horticultural characteristics; however 'SMNMAKTSR' differs in the following:

1. Single and double florets. The comparator has mostly single florets.
2. Magenta pink florets, with centers of double florets colored yellow and green. The comparator has lighter pink solid colored florets.
3. Large lace cap flowers. The comparator has medium lace cap flowers.

BRIEF DESCRIPTION OF THE PHOTOGRAPHS

Figure 1:
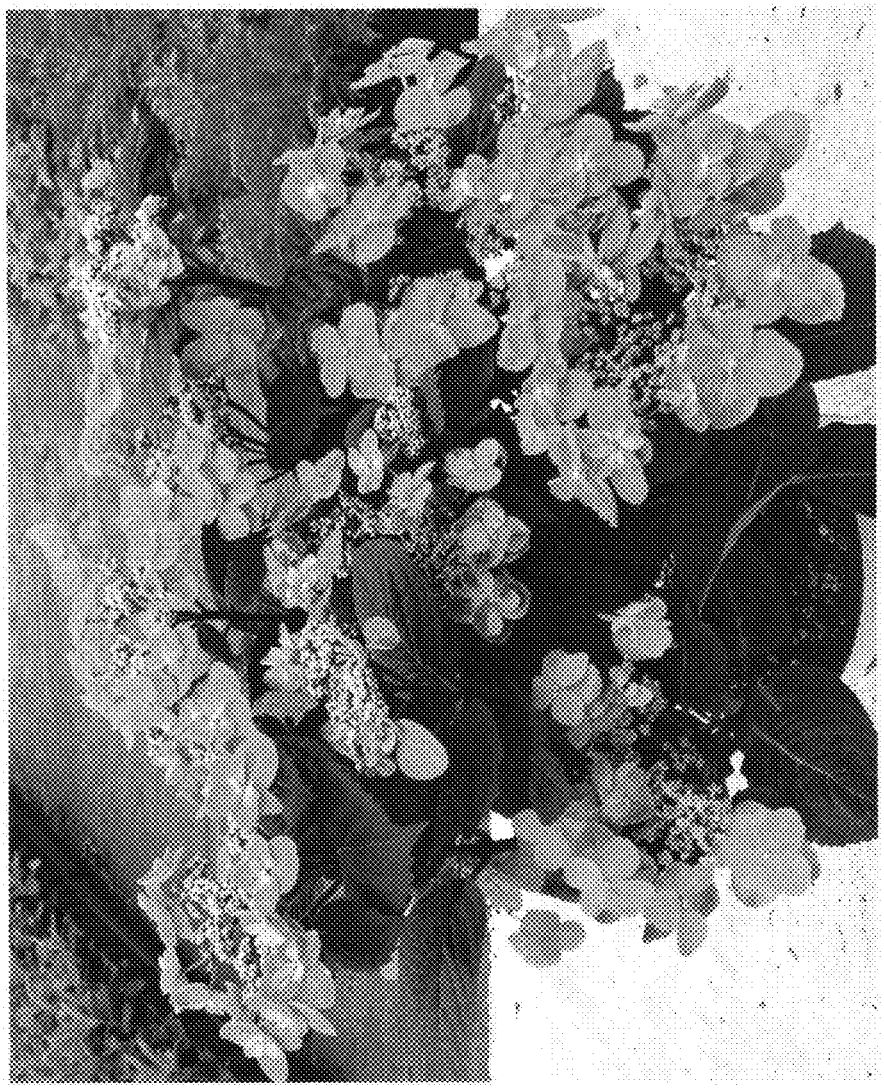

The accompanying photograph in FIG. 1 illustrates in full color a typical plant of 'SMNMAKTSR' grown in a double layered poly greenhouse, in Grand Haven, Mich., in a commercial 3 gallon container. Age of the plant photographed is approximately 3 years.

Figure 2:
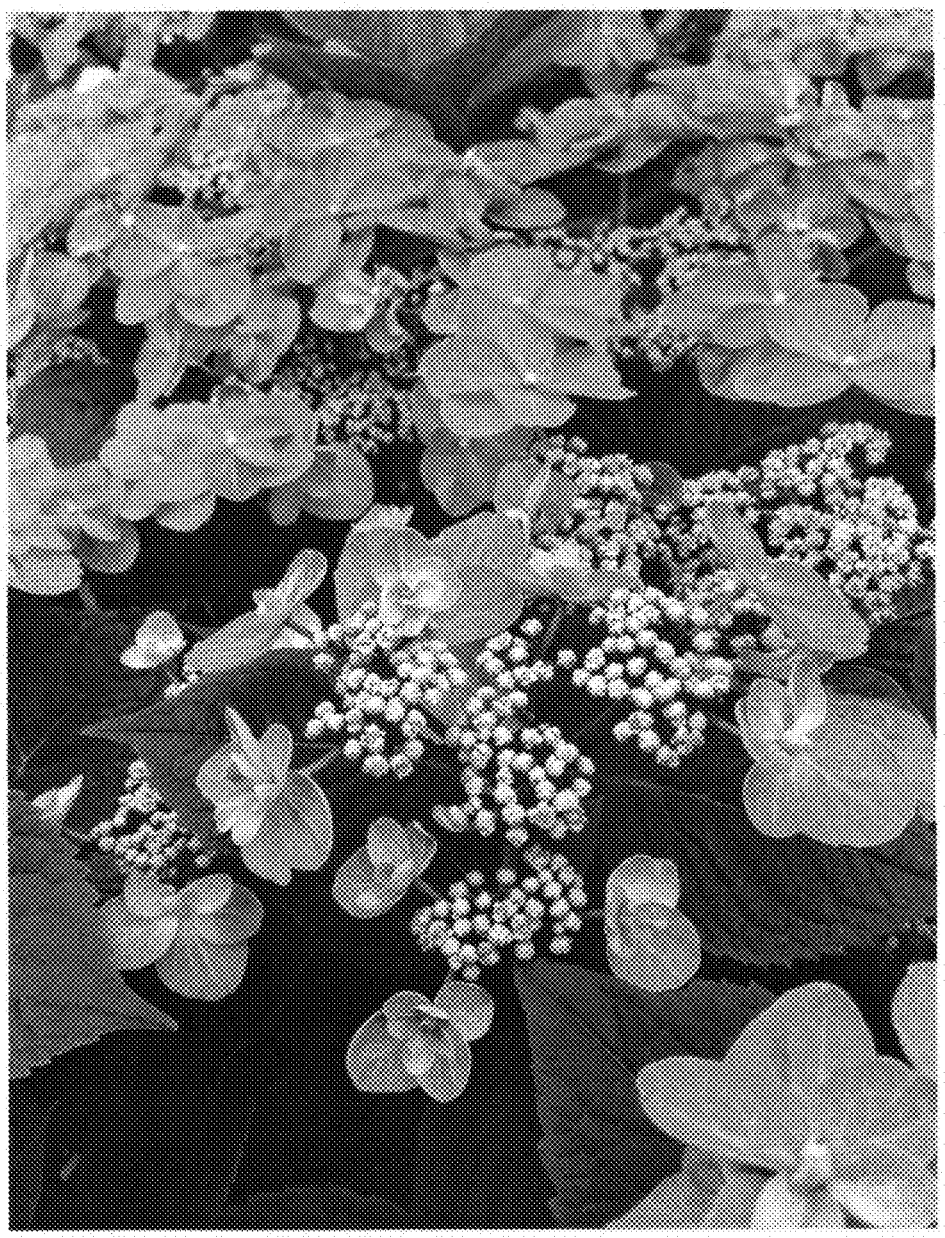

FIG. 2 illustrates typical flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 1995 Royal Horticultural Society Colour Chart except where general terms of ordinary dictionary significance are used. The following observations and measurements describe 'SMNMAKTSR' plants grown in a double layered poly greenhouse, in Grand Haven, Mich. The growing temperature ranged from approximately 18° C. to 27° C. daytime and 5° to 10° C. at night. Measurements and numerical values represent averages of typical plant types. Measurements were taken during April, 2015.

Botanical classification: *Hydrangea* hybrid 'SMNMAKTSR'.

PROPAGATION

Time to initiate roots: Approximately 10 days at approximately 20° C.

Time to produce a rooted young plants: Approximately 30 days at approximately 20° C.

Root description: Medium to thick, white, free to moderate root branching, both fibrous and fleshy.

Propagation method: Softwood cuttings.

PLANT

Age of plant described: 3 years.

Pot size: 3 gallon.

Growth habit: Flowering perennial shrub, mounded in form.

Overall plant shape: Upright, Rounded.

Height: Approximately 40 cm.

Plant spread: Approximately 70 cm.

Growth rate: Strong.

Plant vigor: Strong.

Branching characteristics: Good, lots of basal branches, pinching required.

Length of lateral branches: Approximately 40 cm.

Number of lateral branches: Approximately 20.

Diameter of lateral branches: 0.6-0.8 cm.

Lateral branch shape: Round.

Lateral branch strength: Strong.

Internode length: Average range 4.5-7 cm.

Branch color:

*Immature*.—Near RHS Green 143C.

*Mature*.—Near RHS Yellow-green 144B.

Branch aspect: Upright, outward.

Branch pubescence: None.

Other stem or plant characteristics: Oblong black lenticels.

FOLIAGE

Leaf:

*Arrangement*.—Opposite.

*Average length*.—Approximately 11 cm.

*Average width*.—Approximately 7 cm.

*Shape of blade*.—Ovate-lanceolate.

*Apex*.—Acuminate.

*Base*.—Obtuse.

*Margin*.—Serrulate.

*Texture and appearance of top surface*.—Smooth, glabrous.

*Texture and appearance of bottom surface*.—Slightly pubescent.

*Color*.—Young foliage upper side: Near RHS Green 141A. Young foliage under side: Near RHS Green 141B. Mature foliage upper side: Near RHS Green 135A near stem, fading to Greyed-purple 187A towards margin. Mature foliage under side: Near RHS Green 138A.

*Venation*.—Type: Pinnate. Venation color upper side: Near RHS Greyed-orange 177B. Venation color under side: Near Yellow-Green 145B.

Petiole:

*Average length*.—1-1.5 cm.

*Diameter*.—0.5 cm.

*Color*.—Upper side: Near RHS Greyed-orange 177B to Greyed-orange 166A nearest the stem. Under side: Near RHS Greyed-orange 177B.

*Texture upper side*.—Slightly pubescent, ridged.

*Texture under side*.—Smooth.

FLOWER

Bloom period:

*Natural season*.—Early Summer through Fall. Inflorescence last in good condition approximately 2 months. Plants rebloom Summer through Fall.

Inflorescence:

*Type*.—Lace cap.

*Quantity of flowers per inflorescence*.—Fertile flowers, 250 approximately. Sterile Flowers, 10 to 20 approximately.

*Persistent or self-cleaning*.—Persistent.

*Fragrance*.—No.

Panicle:

*Shape*.—Orbital.

*Height*.—5 cm.

*Diameter*.—9 cm.

Sterile flower:
*Bud shape*.—Orbicular.
*Bud length*.—3 mm.
*Bud diameter*.—3 mm.
*Bud color*.—Near RHS Greyed-purple 186C.
*Flower aspect*.—Upright.
*Flower shape*.—Obovate.
*Flower length*.—3.5 cm.
*Flower diameter*.—3.5 cm.
*Flower depth*.—1.5 cm.
*Other characteristics*.—Very short and somewhat fused.

Sterile flower petals:
*Length of petal*.—Approximately 3 mm.
*Width of petal*.—Approximately 2 mm.
*Apex*.—Acute.
*Shape of petal*.—Ovate.
*Petal margin*.—Entire.
*Petal arrangement*.—Whorled.
*Petal base*.—Acute.
*Petal number*.—6.
*Petals fused*.—No.
*Petal texture*.—Smooth, upper and under side.
*Color*.—Upper surface at first opening: Near RHS Red-purple 70D. Upper surface at maturity: Near RHS Red-purple 72D. Under surface at first opening: Near RHS Red-purple 70D. Under surface at maturity: Near RHS Red-purple 72D.

Sterile flower sepal:
*Arrangement*.—Double or occasionally triple whorl.
*Number*.—Average of 8 to 12 total, arranged in double or triple whorls of 3 to 5. Weak to moderate overlapping.
*Shape*.—Oblong.
*Tip*.—Obovate.
*Base*.—Truncate.
*Margin*.—Entire, with irregular shallow dentations near apex of some sepals.
*Length*.—1.5 cm.
*Width*.—1.75 cm.
*Texture, upper*.—Smooth.
*Texture, lower*.—Smooth.
*Color*.—Upper surface at first opening: Near RHS Yellow-Green 144D, flushed Red-purple 63B. Upper surface at maturity: Near RHS Red-purple 63A, base near Yellow-Green 145C and 144D, colors individually present and mixing together. Outermost whorls produces a yellow green coloration near apex near 144D. Under surface at first opening: Near RHS Red-purple 62C. Under surface at maturity: Near RHS Red-purple 62B. Venation: At opening: Single florets, Upper Surface: Near Yellow-Green 145D. Single florets, Under Surface: Near Yellow-Green 145D. At Maturity: Single florets, Upper Surface: Near White 155D. Single florets, Under Surface: Near Green-White 157A. At opening: Double florets, Upper Surface: Near Yellow 1C. Double florets, Under Surface: Near Yellow-Green 145D. At Maturity: Double florets, Upper Surface: Near Yellow 11D. Double florets, Under Surface: Near White 155D.

Fertile flower:
*Bud shape*.—Orbicular.
*Bud length*.—3 mm.
*Bud diameter*.—3 mm.
*Bud color*.—Near RHS Red-purple 68D.
*Flower aspect*.—Upright.
*Flower shape*.—Orbital.
*Flower length*.—4 mm.
*Flower diameter*.—4 mm.
*Flower depth*.—4 mm.

Fertile flower petals:
*Length of petal*.—2.5 mm.
*Width of petal*.—1 mm.
*Apex*.—Acute.
*Shape of petal*.—Ovate.
*Petal margin*.—Slightly undulate.
*Petal arrangement*.—Whorled.
*Petal number*.—6.
*Petal base*.—Obtuse.
*Petals fused*.—No.
*Petal texture*.—Smooth, upper and under side.
*Color*.—Upper surface at first opening: Near RHS Red-purple 73C. Upper surface at maturity: Near RHS Red-purple 73C. Under surface at first opening: Near RHS Red-purple 73C. Under surface at maturity: Near RHS Red-purple 73C.

Fertile flower pedicel:
*Angle*.—Outward/upright.
*Strength*.—Moderately strong, flexible.
*Length*.—1 cm.
*Width*.—1.5 mm.
*Texture*.—Slightly pubescent.
*Color*.—Near RHS Greyed-red 181B.

Fertile flower sepal:
*Arrangement*.—Whorled.
*Number*.—6.
*Shape*.—Ovate.
*Tip*.—Obtuse.
*Base*.—Obtuse.
*Margin*.—Entire.
*Length*.—1 mm.
*Width*.—1 mm.
*Texture, upper*.—Smooth.
*Texture, lower*.—Smooth.
*Color*.—Upper surface at first opening: Near RHS Yellow-green 144A. Upper surface at maturity: Near RHS Yellow-green 144A. Under surface at first opening: Near RHS Yellow-green 144A. Under surface at maturity: Near RHS Yellow-green 144A.

REPRODUCTIVE ORGANS

Sterile flower:

Androecium:
*Stamen number*.—6.
*Filament length*.—2 mm.
*Filament color*.—Near RHS Yellow-green 145C.
*Anther shape*.—Club-like.
*Anther color*.—Near RHS Yellow-green 145B.
*Anther length*.—1 mm.
*Pollen amount*.—Moderate.
*Pollen color*.—Near RHS Yellow-green 145B.

Gynoecium:
*Pistil number*.—3.
*Pistil length*.—1 mm.
*Stimga shape*.—Flat.
*Stimga color*.—Near RHS Greyed-purple 186B.

*Style length*.—Less than 1 mm.
*Style color*.—Near RHS Greyed-purple 186B.
*Ovary color*.—No ovary.

Fertile flower:

Androecium:

*Stamen number*.—10.
*Filament length*.—3 mm.
*Filament color*.—Near RHS Red-purple 73A.
*Anther shape*.—Club-like.
*Anther length*.—1 mm.
*Anther color*.—Near RHS Greyed-green 196C.
*Pollen amount*.—Moderate.
*Pollen color*.—Near RHS Greyed-green 196C.

Gynoecium:

*Pistil number*.—5-6.
*Pistil length*.—3 mm.
*Stimga shape*.—Club-like.
*Stimga color*.—Near RHS Red-purple 73C.
*Style length*.—1.5 mm.
*Style color*.—Near RHS Red-purple 73C.
*Ovary color*.—Near RHS Yellow-green 145B.

OTHER CHARACTERISTICS

Disease resistance: Neither resistance nor susceptibility to diseases or pests has been observed in this variety.
Temperature tolerance: −25° C. to 37° C.
Fruit/seed production: No fruits/seeds detected to date.
Garden performance: Good tolerance for rain and wind.

What is claimed is:

1. A new and distinct cultivar of *Hydrangea* plant named 'SMNMAKTSR' as herein illustrated and described.

* * * * *